(12) United States Patent
O'Carrol et al.

(10) Patent No.: US 11,865,275 B2
(45) Date of Patent: *Jan. 9, 2024

(54) INTRODUCER SHEATH

(71) Applicant: ABIOMED EUROPE GMBH, Aachen (DE)

(72) Inventors: Ger O'Carrol, Sligo (IE); Thorsten Siess, Aachen (DE); Walid Aboulhosn, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 462 days.

This patent is subject to a terminal disclaimer.

(21) Appl. No.: 16/901,737

(22) Filed: Jun. 15, 2020

(65) Prior Publication Data

US 2020/0306506 A1 Oct. 1, 2020

Related U.S. Application Data

(63) Continuation of application No. 15/541,528, filed as application No. PCT/EP2016/050234 on Jan. 7, 2016, now Pat. No. 10,709,875.

(30) Foreign Application Priority Data

Jan. 7, 2015 (EP) .................................... 15150304

(51) Int. Cl.
*A61M 25/06* (2006.01)
*A61M 25/00* (2006.01)
*A61M 39/06* (2006.01)

(52) U.S. Cl.
CPC .... *A61M 25/0668* (2013.01); *A61M 25/0097* (2013.01); *A61M 39/06* (2013.01); *A61M 25/0074* (2013.01); *A61M 2025/0675* (2013.01)

(58) Field of Classification Search
CPC .......... A61M 25/0668; A61M 25/0097; A61M 39/06; A61M 25/0074; A61M 2025/0675; A61M 2039/062; A61B 17/34
See application file for complete search history.

(56) References Cited

U.S. PATENT DOCUMENTS 4,687,469 A * 8/1987 Osypka .................. A61N 1/056
604/161
4,699,611 A 10/1987 Bowden
(Continued)

FOREIGN PATENT DOCUMENTS

CN 101060873 A 10/2007
CN 101918064 A 12/2010
(Continued)

OTHER PUBLICATIONS

Office Action from corresponding Japanese Application No. 2020-173636 dated Feb. 22, 2022 (8 pages).
(Continued)

*Primary Examiner* — Theodore J Stigell
(74) *Attorney, Agent, or Firm* — Botos Churchill IP Law LLP (57) ABSTRACT

An introducer sheath for providing access in a patient's body comprises a tubular body with a distal portion and a proximal portion, the proximal portion being configured to be inserted into the patient's body to allow a medical device to be inserted through the introducer sheath into the patient's body. In order for the introducer sheath to be removable from the patient, it can be separated along its length in a longitudinal direction. The introducer sheath further comprises at least a first handle which is pivotable about a fulcrum. The first handle has a first end portion and a free second end portion so as to form a lever, such that pivoting the handle about the fulcrum causes a contacting portion of the handle to act on a respective counter portion that is
(Continued)

operatively connected to the distal portion of the tubular body. This creates a breaking force that causes the distal portion of the tubular body to break.

9 Claims, 9 Drawing Sheets

(56) References Cited

U.S. PATENT DOCUMENTS

| | | | |
|---|---|---|---|
| 5,139,486 A | 8/1992 | Moss | |
| 5,167,634 A | 12/1992 | Corrigan et al. | |
| 5,234,425 A | 8/1993 | Fogarty et al. | |
| 5,304,142 A | 4/1994 | Liebl et al. | |
| 5,320,611 A | 6/1994 | Bonutti et al. | |
| 5,322,512 A * | 6/1994 | Mohiuddin | A61M 25/0668 604/177 |
| 5,395,341 A | 3/1995 | Slater | |
| 5,397,310 A | 3/1995 | Chu et al. | |
| 5,407,430 A | 4/1995 | Peters | |
| 5,488,960 A | 2/1996 | Toner | |
| 5,489,273 A | 2/1996 | Whitney et al. | |
| 5,492,530 A | 2/1996 | Fischell et al. | |
| 5,536,255 A | 7/1996 | Moss | |
| 5,573,517 A | 11/1996 | Bonutti et al. | |
| 5,653,697 A | 8/1997 | Quiachon et al. | |
| 5,911,702 A | 6/1999 | Romley et al. | |
| 5,935,122 A | 8/1999 | Fourkas et al. | |
| 5,971,993 A | 10/1999 | Hussein et al. | |
| 6,197,016 B1 | 3/2001 | Fourkas et al. | |
| 6,338,730 B1 | 1/2002 | Bonutti et al. | |
| 6,428,556 B1 | 8/2002 | Chin | |
| 6,562,049 B1 | 5/2003 | Norlander et al. | |
| 6,613,038 B2 | 9/2003 | Bonutti et al. | |
| 6,692,462 B2 | 2/2004 | Mackenzie et al. | |
| 6,814,715 B2 | 11/2004 | Bonutti et al. | |
| 6,887,417 B1 | 5/2005 | Gawreluk et al. | |
| 7,025,746 B2 | 4/2006 | Tal | |
| 7,422,571 B2 | 9/2008 | Schweikert et al. | |
| 7,524,305 B2 | 4/2009 | Moyer | |
| 7,722,567 B2 | 5/2010 | Tal | |
| 7,887,733 B2 * | 2/2011 | Moyer | A61B 17/3421 264/273 |
| 8,147,452 B2 | 4/2012 | Nardeo et al. | |
| 8,597,277 B2 | 12/2013 | Lenker et al. | |
| 8,672,888 B2 | 3/2014 | Tal | |
| 8,758,402 B2 | 6/2014 | Jenson et al. | |
| 9,884,169 B2 | 2/2018 | Bierman et al. | |
| 10,709,875 B2 * | 7/2020 | O'Carrol | A61M 25/0097 |
| 2003/0088264 A1 | 5/2003 | Spohn et al. | |
| 2004/0064147 A1 | 4/2004 | Struble | |
| 2004/0098020 A1 * | 5/2004 | Nardeo | A61M 29/00 606/194 |
| 2005/0049628 A1 | 3/2005 | Schweikert et al. | |
| 2005/0149105 A1 | 7/2005 | Leeflang et al. | |
| 2006/0135981 A1 | 6/2006 | Lenker et al. | |
| 2006/0287574 A1 | 12/2006 | Chin | |
| 2008/0046005 A1 | 2/2008 | Lenker et al. | |
| 2008/0051734 A1 | 2/2008 | Bonutti et al. | |
| 2008/0051821 A1 | 2/2008 | Gephart | |
| 2008/0082165 A1 | 4/2008 | Wilson et al. | |
| 2009/0143739 A1 | 6/2009 | Nardeo et al. | |
| 2009/0177163 A1 | 7/2009 | King et al. | |
| 2009/0192463 A1 | 7/2009 | Nardeo et al. | |
| 2009/0240202 A1 | 9/2009 | Drasler et al. | |
| 2010/0268196 A1 | 10/2010 | Hastings et al. | |
| 2013/0131718 A1 | 5/2013 | Jenson et al. | |
| 2013/0310765 A1 | 11/2013 | Stephens et al. | |
| 2013/0317438 A1 | 11/2013 | Ellingwood et al. | |
| 2013/0317481 A1 | 11/2013 | Ellingwood et al. | |
| 2014/0025003 A1 | 1/2014 | Kimmel et al. | |
| 2015/0151086 A1 | 6/2015 | Teoh | |
| 2016/0066948 A1 | 3/2016 | Ellingwood et al. | |
| 2016/0220358 A1 | 8/2016 | Wilson et al. | |
| 2016/0354583 A1 | 12/2016 | Ellingwood et al. | |
| 2017/0056063 A1 | 3/2017 | Ellingwood et al. | |
| 2017/0238965 A1 | 8/2017 | Murphy | |
| 2017/0281908 A1 | 10/2017 | Ellingwood et al. | |

FOREIGN PATENT DOCUMENTS

| | | |
|---|---|---|
| EP | 1444000 A2 | 8/2004 |
| EP | 2335764 A1 | 6/2011 |
| EP | 2623151 A1 | 8/2013 |
| EP | 3311873 A1 | 4/2018 |
| JP | H02102667 A | 4/1990 |
| JP | 2004514506 A | 5/2004 |
| JP | 2008509782 A | 4/2008 |
| JP | 2008514286 A | 5/2008 |
| JP | 2011510686 A | 4/2011 |

OTHER PUBLICATIONS

Office Action in corresponding Chinese Patent Application No. 202010768352.7 dated Nov. 29, 2021, 18 pp.
Extended European Search Report EP 17 75 7090 dated Jul. 9, 2019 (3 pages).
International Search Report PCT/EP2016/050234 dated May 20, 2016 (5 pages).
Office Action from corresponding Korean Application No. 10-2017-7021923 dated Sep. 29, 2022 (14 pp.).

* cited by examiner

INTRODUCER SHEATH

CROSS-REFERENCE TO RELATED APPLICATIONS

This application is a continuation of U.S. application Ser. No. 15/541,528, filed Jul. 5, 2017, allowed, which application is a United States National Stage filing under 35 U.S.C. § 371 of International Application No. PCT/EP2016/050234, filed Jan. 7, 2016, which claims the benefit of European Patent Application No. 15150304.2, filed Jan. 7, 2015, the contents of all of which are incorporated by reference herein in their entirety. International Application No. PCT/EP2016/050234 published under PCT Article 21(2) in English.

BACKGROUND

Long term vascular access is a common medical procedure used in several medical situations including dialysis for patients requiring frequent dialysis treatments, chemotherapy treatment or ventricular assist device use. Different devices and different methods are used depending on patient needs. Long term vascular access in patients needing ventricular assist devices is common through an open chest procedure and direct cardiovascular access.

Lately there has been a move toward the use of peripheral vessels to access the cardiovascular system in order to avoid traumatic open chest surgery. The move toward the use of peripheral vessels instead of central cardiovascular vessels has been accompanied by the development of a large number of specific devices and tools that are specifically designed for peripheral use. Vascular introducers are the most common devices that have been developed to allow peripheral vascular access. For providing access to a vessel, an introducer sheath usually is directly pierced into a vessel, in particular with the help of a dilator.

Once a medical device, such as a catheter, has been inserted through the introducer sheath into a patient's vessel, the introducer sheath usually is no longer needed and it is desired to remove it. However, since the medical device may be connected to a device external to the patient's body, such as a power source, the introducer sheath cannot be simply retracted but has to be peeled away from the medical device. Commonly, the introducer sheath is separated along its length in a longitudinal direction so that the resulting pieces can be removed from the patient. In order to assist in splitting the introducer sheath, handles may be provided that can be gripped by a user, for example a surgeon, to apply a breaking force. Usually, a hemostatic valve at the distal portion of the introducer sheath has to be broken, which requires a high initial force. This cumbersome procedure can cause difficulties and harm to the patient, for instance if the medical device is inadvertently retracted when the handles are actuated to apply the breaking force.

SUMMARY OF THE INVENTION

It is an objective of the present invention to provide an introducer sheath for providing access to a patient's body that can be separated along its length, wherein handling is improved and in particular a breaking force that has to be applied by a user to split the introducer sheath is reduced.

The invention is described in the accompanying independent claims, with preferred embodiments being specified in the dependent claims.

According to one embodiment of the invention, an introducer sheath for providing access in a patient's body is provided, in particular transcutaneous access, more specifically vascular access. The introducer sheath comprises a tubular body with a distal portion and a proximal portion, the proximal portion being configured to be inserted into the patient's body, such as a vessel or other body cavity, to allow a medical device to be inserted through the introducer sheath into the patient's body. For instance, the medical device may be inserted into a patient's vessel and may be a catheter that may be connected to an axial blood pump. In other cases, the introducer sheath may be a cannula of a trocar. The introducer sheath is structured to facilitate separation along its length in a longitudinal direction. For example, at least the distal portion of the tubular body may comprise a structure, such as a longitudinal notch, forming a predetermined breaking line. It is to be understood that the term "proximal" refers to directions towards the heart, while the term "distal" refers to directions away from the heart.

The introducer sheath further comprises at least one handle which is pivotable about a fulcrum, the handle having a first end portion and a free second end portion so as to form a lever. Pivoting the handle about the fulcrum causes a contacting portion of the handle to act on a respective counter portion that is operatively connected to the distal portion of the tubular body, thereby creating a breaking force that causes the distal portion of the tubular body to break, split or crack. Due to the lever principle, the pivotable handle allows for a reduction of the force that has to be applied by a user to break the introducer sheath. Not only is the force reduced, the general handling during separation of the introducer sheath is also improved, in particular with respect to ergonomic aspects, for instance movement and position of the hands and arms of a user. This results from the fact that, in contrast to a handle that is fixedly and directly attached to the tubular body of the introducer sheath, a pivotable handle transmits the force applied by a user to the introducer sheath indirectly.

In an embodiment, the fulcrum is disposed eccentrically in the first end portion of the handle and the contacting portion is disposed at an edge of the first end portion, wherein a distance between the contacting portion and the fulcrum is less than a distance between the free second end portion of the handle and the fulcrum to utilize the lever principle. Preferably, a distance between the fulcrum and the contacting portion is larger than a distance between the fulcrum and a portion of the edge of the first end portion adjacent the contacting portion. The edge of the first end portion of the handle may be specifically shaped, for example curved. In other words, pivoting the handle moves the contacting portion of the handle towards the counter portion and pushes away the counter portion when pivoting, i.e. in particular pushing or pulling, of the handle is continued. The contacting portion may already contact the counter portion in a neutral position, i.e. in an unstressed condition, or may come into contact only when the handle is pivoted. Due to the shape of the contact portion, the counter portion is pushed away until the distal portion of the introducer sheath breaks.

In an alternative embodiment, the fulcrum is disposed between the first and second end portions and the contacting portion is disposed at an edge of the first end portion. In another alternative embodiment, the contacting portion is disposed between the first and second end portions and the fulcrum is disposed in the first end portion.

Generally, it is sufficient if only a single handle is provided to create the breaking force. However, handling may be improved if another handle is provided. Thus, the introducer sheath may comprise at least one further handle, wherein—if two handles are provided—the two handles are preferably diametrically opposed with respect to the tubular body. The further handle may be fixedly attached to the distal portion of the tubular body, or both handles may be pivotably attached to the distal portion of the tubular body. Possibly, more than two handles, for example three or four handles, may be provided that can be arranged symmetrically about the tubular body of the introducer sheath. It will be appreciated that an asymmetrical arrangement is possible, too. It shall be understood that all features described for a single handle or one of the handles may also apply to the further handle or all handles in embodiments where two or more handles are provided.

The counter portion may be disposed on and particularly be part of the distal portion of the introducer sheath. Alternatively, in embodiments having two handles, the counter portion associated with one of the handles may be the contacting portion of the other one of the handles and preferably vice versa. In other words, the contacting portions of the two handles may act on each other such that a breaking force is applied to the distal portion of the introducer sheath.

The handle or handles may be pivotably attached to the distal portion of the tubular body via a hinge, wherein the hinge preferably comprises at least one pin arranged along the fulcrum and at least one cavity that receives the pin. It will be appreciated that the handles may be pivotably attached to the tubular body of the introducer sheath in other ways.

The handle, in an unstressed condition, i.e. in a neutral condition without application of an external force, may extend from the distal portion of the tubular body of the introducer sheath at different angles. In case two handles are provided, the handles may extend from the introducer sheath symmetrically, i.e. at same angles. However, the two handles may also extend at different angles. The handle may extend from the introducer sheath at an angle between 45° and 90° or at an angle less than 45°. Preferably, the angle ranges between 60° and 80° or between 10° and 30°. In case the angle is unequal to 90°, the handle may point towards either the distal end or the proximal end of the body of the introducer sheath.

The handle may be either pushed or pulled by a user. In other words, the handle may be pivotably attached to the distal portion of the tubular body such that pivoting in a direction towards or away from the proximal portion of the tubular body causes the distal portion to break. Pushing the handle, that is to say, pivoting the handle towards the proximal end portion, may be advantageous because pulling the handle could lead to an inadvertent retraction of the introducer sheath from the patient's vessel, which might cause problems because the introducer sheath cannot be pushed back into the vessel.

In a preferred embodiment, the handle or handles may be secured or locked to prevent inadvertent actuation. For this purpose, the handle may comprise an engagement portion configured to engage a locking member such that the handle is prevented from pivoting. The locking member may be provided separately or may be comprised in the introducer sheath, wherein the locking member can be manipulated to be in or out of engagement with the engagement portion of the handle. The locking member may be engageable with the engagement portion of the handle by means of threads, a hook, a clip or any other appropriate engagement means. The locking member may be a locking cap. For example, the locking member may be rotated to secure or release the handle. It will be appreciated that the locking member may also be part of a dilator that is inserted into the introducer sheath.

In an embodiment, the introducer sheath comprises a hemostatic valve in the distal portion of the tubular body. The hemostatic valve provides hemostasis. In other words, it seals the distal end of the introducer sheath to prevent blood from flowing through the valve during insertion of a medical device, such as a catheter. The valve may include a membrane that may be constructed as a flexible disk or in another configuration providing the function of a check valve. The at least one handle preferably is attached to the hemostatic valve such that the breaking force can be applied directly to the valve so as to split the valve. Splitting the valve usually requires the highest force during separation of the introducer sheath.

In an embodiment, the first handle has a handle axis passing through the fulcrum and the free second end portion, and intersecting the longitudinal axis of the sheath.

BRIEF DESCRIPTION OF THE DRAWINGS

The foregoing summary, as well as the following detailed description of preferred embodiments, are better understood when read in conjunction with the appended drawings. For the purpose of illustrating the present disclosure, reference is made to the drawings. The scope of the disclosure is not limited, however, to the specific embodiments disclosed in the drawings. In the drawings:

FIGS. 3a to 4b show side views of alternative embodiments of an introducer sheath in initial positions (FIGS. 3a and 4a) and actuated positions (FIGS. 3b and 4b), respectively.

DETAILED DESCRIPTION

Figure 1:
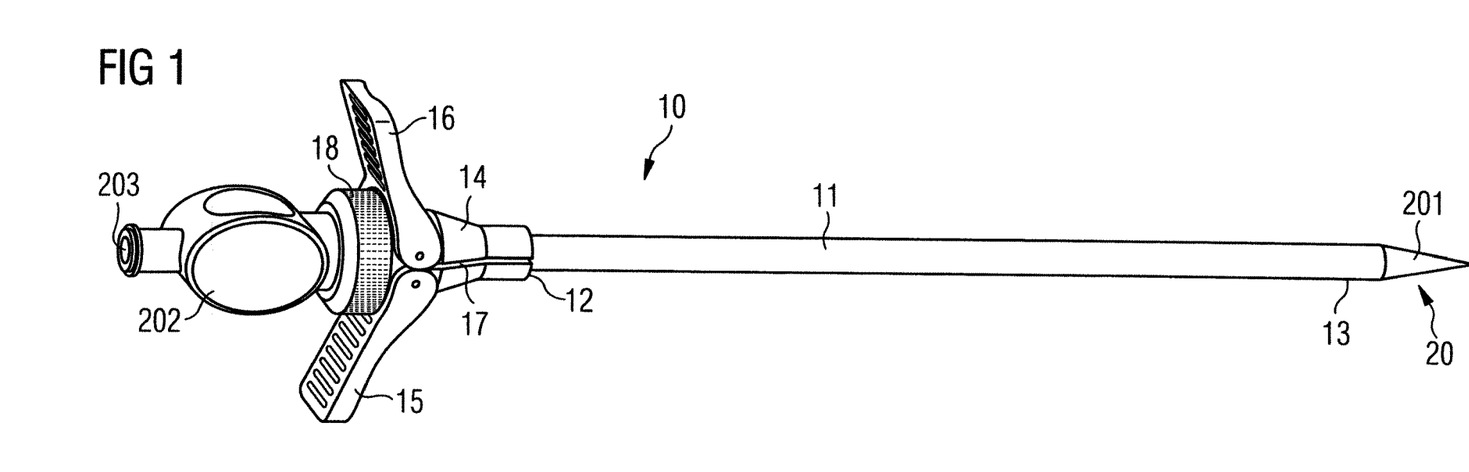
FIG. 1 shows an embodiment of an introducer sheath assembled on a dilator.

Referring to FIG. 1, an introducer sheath 10 according to an embodiment is shown assembled on a dilator 20. A tapered tip 201 of the dilator 20 extends proximally of the introducer sheath 10. A distal end portion 202 of the dilator can be gripped to manipulate the assembly and may include a port 203 for example for a guide wire. The dilator and introducer sheath assembly can be inserted into a patient's vessel that has been accessed for example by means of the Seldinger technique. In other embodiments, the assembly could be a trocar having a cannula and an obturator for providing access to other body cavities. The introducer sheath 10 has a tubular body 11 with the distal portion 12 and a proximal portion 13. A hemostatic valve 14 is arranged in the distal portion 12 of the tubular body 11 to provide hemostasis, i.e. to prevent blood from flowing out of the introducer sheath 10 when inserted in a patient's vessel. In one embodiment the hemostasis valve may be made of two or more separate pieces that, when assembled inside a hemostasis shell, will create a fluidic tight seal preventing blood from flowing back. The hemostasis valve may be a "silicone gland".

Once a medical device, such as a catheter, has been inserted through the introducer sheath 10 after retraction of the dilator 20, it is desired to remove the introducer sheath 10 from the patient. Due to the presence of the medical device, however, the introducer sheath 10 cannot be retracted but has to be separated and peeled away from the medical device. While the tubular body 11 of the introducer sheath 10 can be torn along its length with a relatively low force, the hemostasis valve 14 has to be cracked with a relatively high force. In order to allow splitting of the hemostasis valve 14, the valve 14 is provided with longitudinal notches 17 (only one being visible in FIG. 1; a single notch may also be possible) on opposing sides of the hemostasis valve 14, forming predetermined breaking lines. Handles 15 and 16 are provided to apply a breaking force to the hemostasis valve 14 to initiate splitting of the valve 14. A locking cap or safety cap 18 is provided to prevent the handles 15 and 16 from inadvertent actuation, as described in more detail below. While it is preferred in this embodiment that both handles 15, 16 are pivotable, one of the handles may be fixed, or even only a single handle may be provided.

Figure 2A:
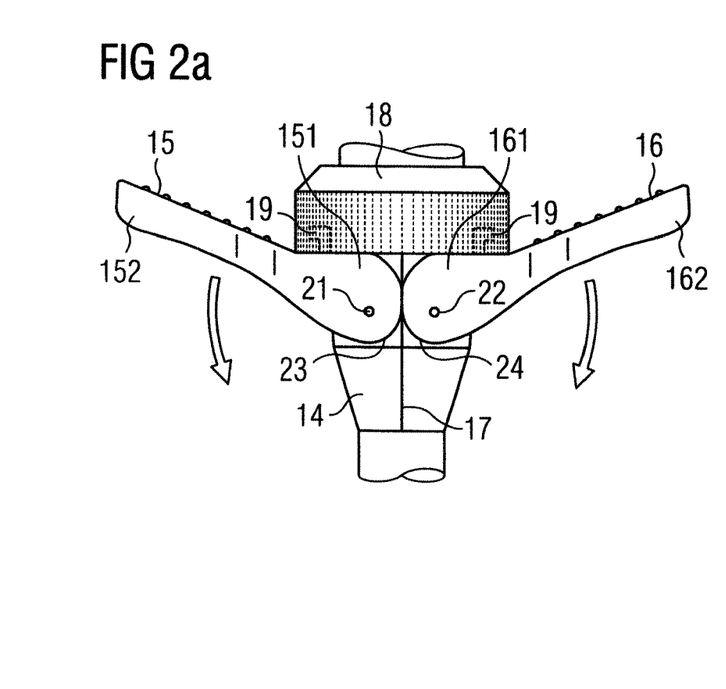
FIG. 2a shows a side view of a distal portion of the introducer sheath of FIG. 1 in an initial position.
Figure 2B:
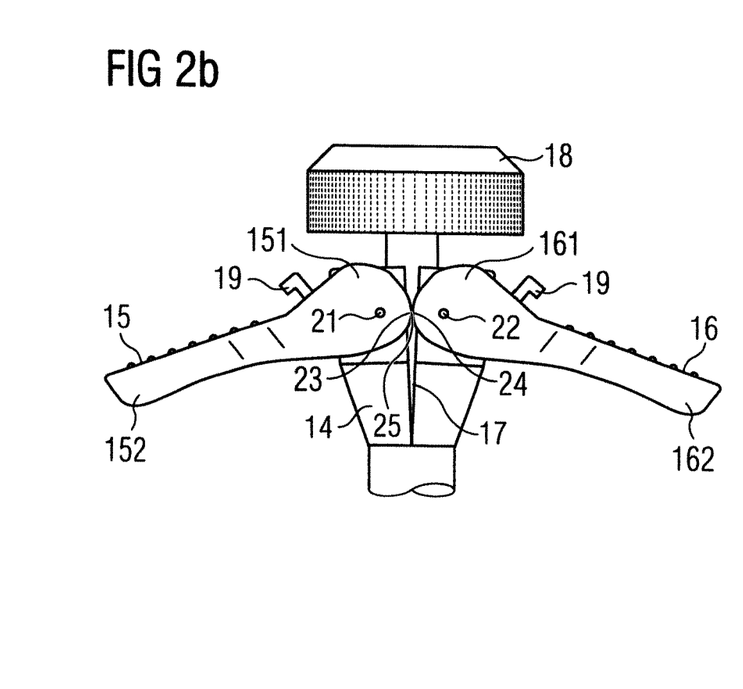
FIG. 2b shows a side view of a distal portion of the introducer sheath of FIG. 1 in an actuated position.

FIGS. 2a and 2b show a side view of the distal portion 12 of the introducer sheath 10 of FIG. 1 including the hemostasis valve 14, the handles 15 and 16 and the locking cap 18. The handles 15 and 16 have respective first end portions 151 and 161 and free second end portions 152 and 162. They extend from the hemostasis valve 14 at an angle of about 70° and point away from the proximal portion 13 of the body 11 of the introducer sheath 10. The handles 15 and 16 are pivotably attached to the hemostasis valve 14, for example by means of a hinge, as described in more detail below with respect to FIGS. 6a to 6c. The handles 15 and 16 each form a lever and are pivotable about a fulcrum 21 and 22, respectively, in particular pivotable towards the proximal portion 13 of the body 11 of the introducer sheath 10 as indicated by the arrows in FIG. 2a.

The handles 15 and 16 have an engagement portion 19, such as a hook, that is engageable with the locking cap 18. For instance, the locking cap 18 may have inner threads that engage the hooks 19 or may engage the hooks like a bayonet coupling. The locking cap 18 particularly prevents inadvertent actuation of the handles 15 and 16 during insertion of the introducer sheath 10 when assembled on a dilator 20 as shown in FIG. 1. During this stage of the procedure the handles 15 and 16 may be used to assist in insertion of the assembly and it would not be desirable but harmful to split the hemostasis valve 14 at this point of time.

When the surgeon decides to remove the introducer sheath 10 from the patient, the introducer sheath 10 has to be separated into two pieces and peeled away from a medical device that has been inserted through the introducer sheath 10. The surgeon may then release the locking cap 18 such that the handles 15 and 16 are operable. In this embodiment, the handles 15 and 16 can be pushed down to the proximal portion 13 of the tubular body 11 of the introducer sheath 10. The actuated position is shown in FIG. 2. The handles 15 and 16 are pivoted about the respective fulcrum 21 and 22 such that the contact portions 23 and 24 act on each other to cause a breaking force that cracks the hemostasis valve 14. The location where the contacting portions 23 and 24 act on each other is indicated at reference number 25 in FIG. 2b. In this embodiment, the contacting portions 23 and 24 function as respective counter portions. The contacting portion 23 of the handle 15 functions as the counter portion for the contacting portion 24 of the handle 16, while the contacting portion 24 of the handle 16 functions as the counter portion for the contacting portion 23 of the handle 15. Because of the eccentric positions of the fulcrums 21 and 22 in the end portions 151 and 161 of the handles 15 and 16 and the specifically shaped edges of the end portions 151 and 161, the contacting portions 23 and 24 are forced away from each other as the handles 15 and 16 are pivoted to create a breaking force that cracks the hemostasis valve 14 along the notch 17. Due to the lever principle the force that has to be applied by the surgeon to create the breaking force is reduced. The pivotable handles facilitate handling compared to fixedly attached handles.

Figure 3A:
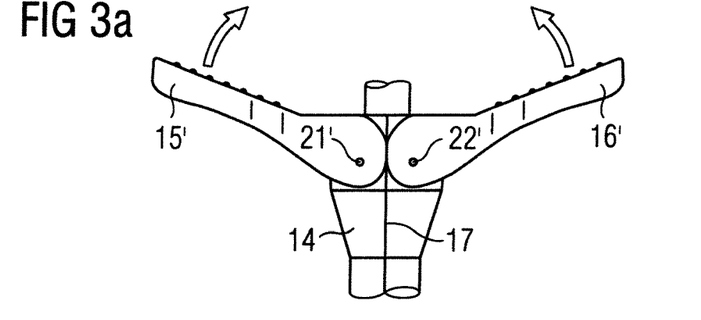
Figure 3B:
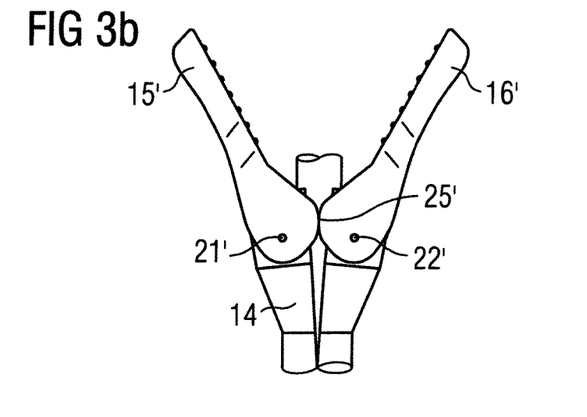

FIGS. 3a and 3b show another embodiment of the handles 15' and 16' which is similar to the above-described embodiment with the exception that the handles 15' and 16' are pivotable away from the proximal portion 13 of the body 11 of the introducer sheath 10 to create the breaking force. As shown in FIG. 3a, the initial position is substantially the same as in the embodiment of FIG. 2a. However, FIG. 3b shows that the handles 15' and 16' are pivoted about the fulcrums 21' and 22' in the opposite direction compared to the embodiment of FIG. 2b and act on each other at point 25' to create the breaking force that cracks the hemostasis valve 14 along the notch 17.

Figure 4A:
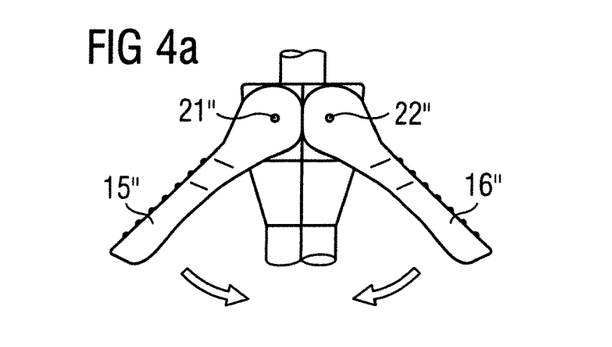
Figure 4B:
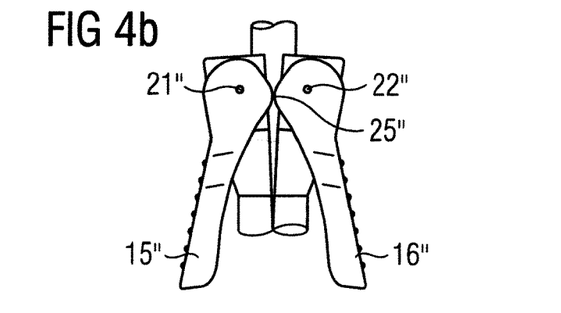

Another embodiment is shown in FIGS. 4a and 4b which is similar to the above-described embodiments. As in the embodiment of FIGS. 2a and 2b, the handles 15" and 16" are pivotable about respective fulcrums 21" and 22" towards the proximal portion 13 of the body 11 of the introducer sheath 10 to create a breaking force that cracks the hemostasis valve 14. However, in an unstressed condition the handles 15" and 16" extend from the hemostasis valve 14 at a different angle compared to the other embodiments, namely a smaller angle where the handles 15" and 16" are closer to the tubular body 11. In this "low-profile configuration" the handles 15" and 16" only have to be pressed together to crack the hemostasis valve 14. In this embodiment, the handles 15" and 16" are moved only by a short distance compared to the other embodiments. This, however, is sufficient to at least initially split the hemostasis valve 14, and may be advantageous because the risk of retracting the introducer sheath 10 can be reduced. The surgeon can complete separation of the introducer sheath 10 by manually tearing and peeling away the introducer sheath 10 from an inserted medical device.

Figure 5:
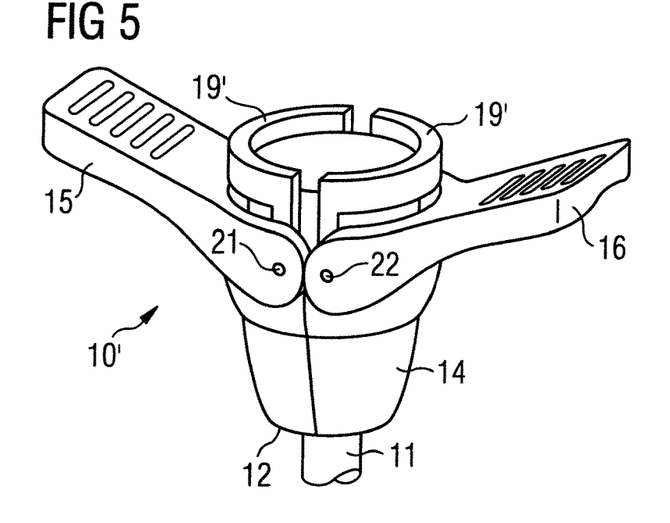
FIG. 5 shows another embodiment of an introducer sheath.
Figure 7:
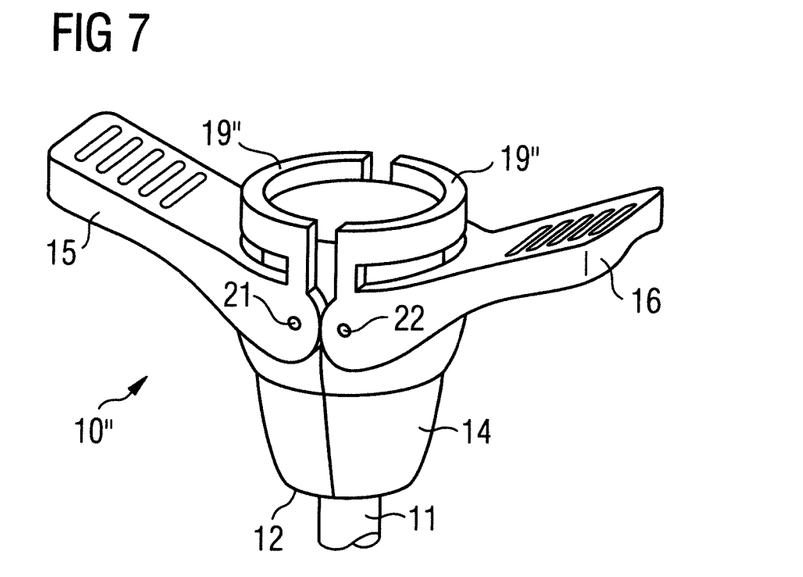
FIG. 7 shows another embodiment of an introducer sheath.

FIG. 5 shows another embodiment of an introducer sheath 10' which is similar to the embodiment of FIGS. 1, 2a and 2b. The only difference is the shape of the engagement portion 19' that can be engaged by the locking cap 18 (not shown) to secure the handles 15 and 16 and prevent them from pivoting. In the embodiment of FIG. 5, the engagement portions 19' have a semicircular shape and are formed as pieces separate from the handles 15 and 16, for instance injection molded pieces. In the embodiment of the introducer sheath 10" shown in FIG. 7, the engagement portions 19'" are formed integrally with the handles 15 and 16.

Figure 6A:
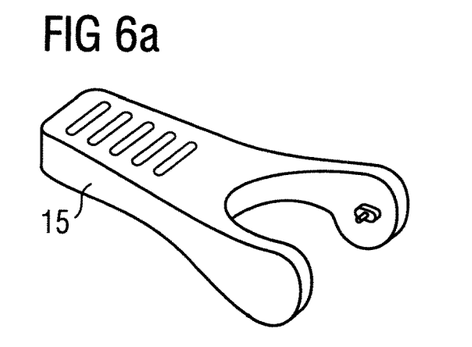
FIGS. 6a to 6c show details of the embodiment of FIG. 5.
Figure 6B:
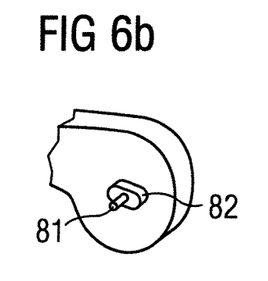
Figure 6C:
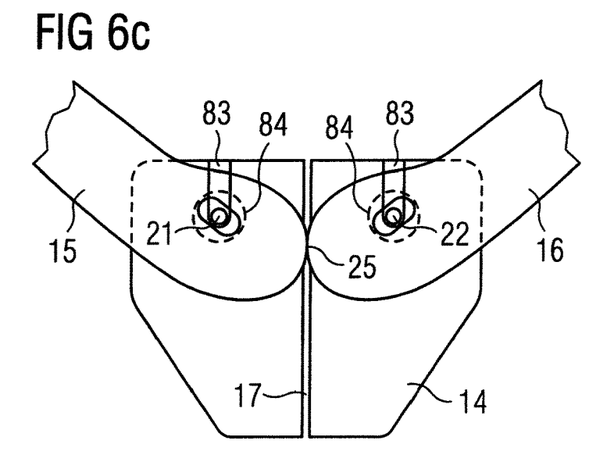

FIGS. 6a to 6c show details of the hinge connection between the handles 15 and 16 and the hemostasis valve 14. Generally, the hinge comprises a pin 81 that is rotatably received in a cavity 84 to allow the handles 15 and 16 to be pivoted about the fulcrums 21 and 22, respectively. The hinge further comprises a base portion 82 that has an elongated shape and supports the pin 81. As shown in FIG. 6c, the base portions 82 prevent the handles 15 and 16 from falling off the hemostasis valve 14. Slots 83 are provided to access the cavities 84. The slots 83 have a width corresponding to the width of the base portions 82 to allow the base portions 82 to be inserted into the slots 83 only in a certain orientation in which the elongate base portions 82 are aligned with the slots 83.

Figure 8:
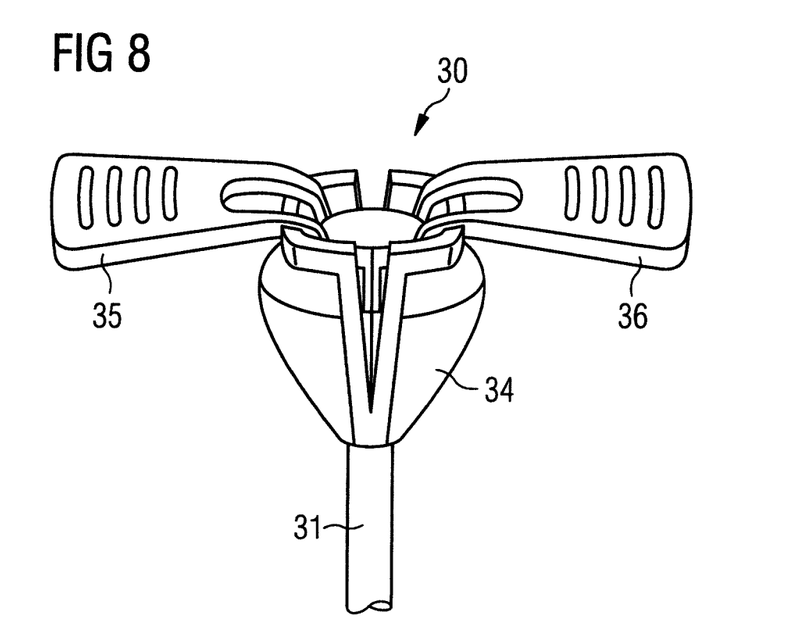
FIG. 8 shows another embodiment of an introducer sheath.
Figure 9A:
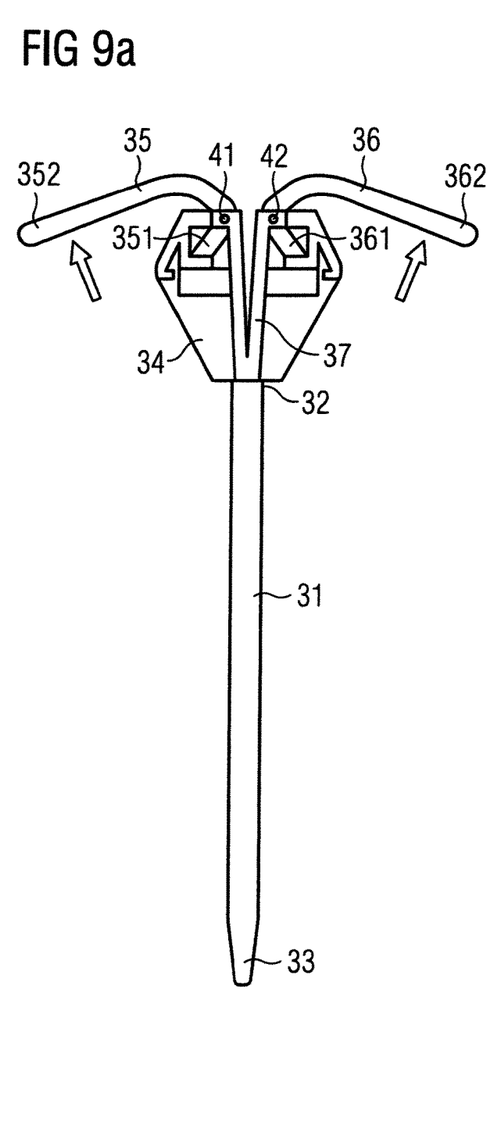
FIGS. 9a and 9b show sectional views of the introducer sheath of FIG. 8 in an initial position and an actuated position, respectively.
Figure 9B:
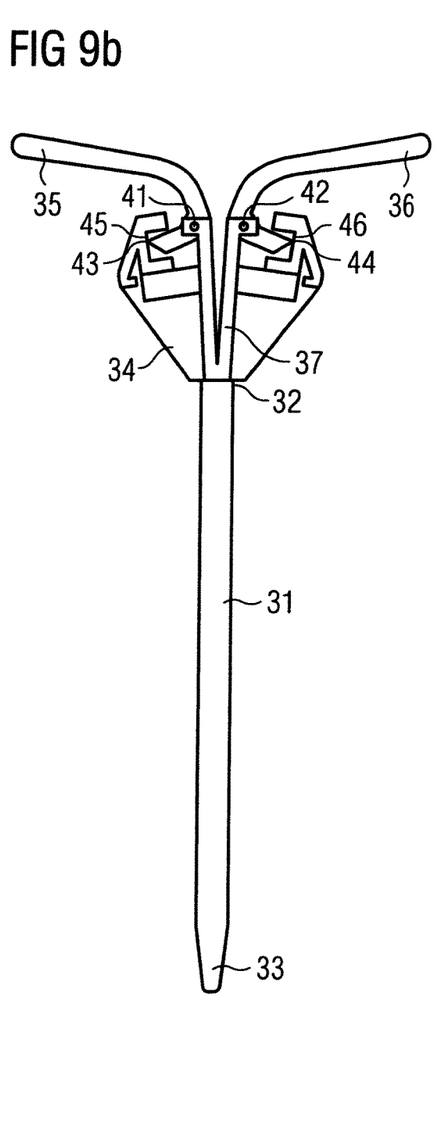

Another embodiment of an introducer sheath 30 is shown in FIGS. 8, 9a and 9b. The introducer sheath 30 has a tubular body 31 and a hemostasis valve 34 disposed at the distal portion 32 of the body 31. Handles 35 and 36 are pivotably attached to the hemostasis valve 34 to aid in splitting the hemostasis valve 34. In contrast to the previously described embodiments, the handles 35 and 36 do not contact each other and do not act on each other to create a breaking force. Instead, the handles 35 and 36 are pivotably attached to a fixed frame portion 37 by means of hinges that form respective fulcrums 41 and 42. In this embodiment, the fulcrums 41 and 42 are disposed between first end portions 351 and 361 and second end portions 352 and 362 of the handles 35 and 36, respectively. The first end portions 351 and 361 are bent, with contact portions 43 and 44 contacting respective counter portions 45 and 46 that are disposed in the hemostasis valve 34. Pulling the handles 35 and 36 in a direction away from the proximal portion 33 of the body 31 of the introducer sheath 30 creates a force that pushes the respective counter portions 45 and 46 away from the frame portion 37 to crack the hemostasis valve 34. In this embodiment, both handles 35 and 36 act independently.

Figure 10A:
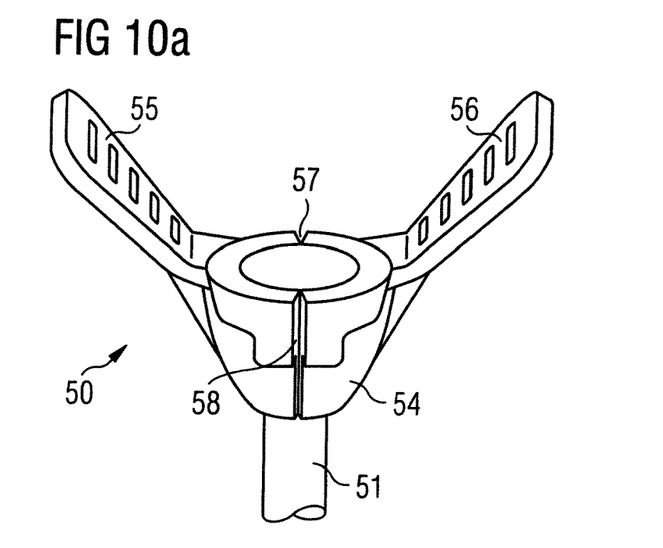
FIGS. 10a to 10c show another example of an introducer sheath in different views.
Figure 10B:
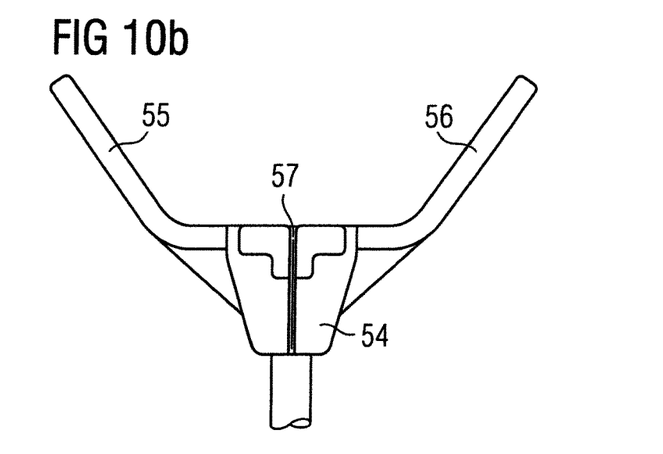
Figure 10C:
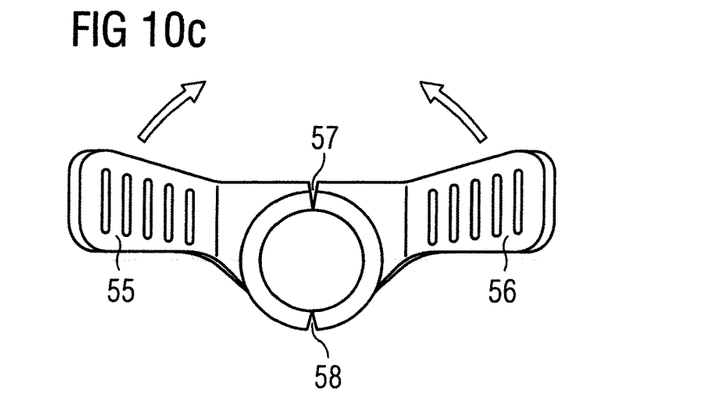

An example of an introducer sheath 50 having a tubular body 51 and a hemostasis valve 54 that can be separated by means of handles 55 and 56 is disclosed in FIGS. 10a to 10c. In this embodiment, the handles 55 and 56 are used to apply a torsional force to crack the hemostasis valve 54, as indicated by the arrows in FIG. 10c. Longitudinal notches 57 and 58 facilitate splitting of the hemostasis valve into two pieces. As becomes apparent from FIGS. 10b and 10c, the handles extend from the hemostasis valve at an angle of 45° and are designed asymmetrically in top view to facilitate handling, in particular to provide a space between the patient's body and the handles 55 and 56 for gripping the handles 55 and 56.

Figure 11A:
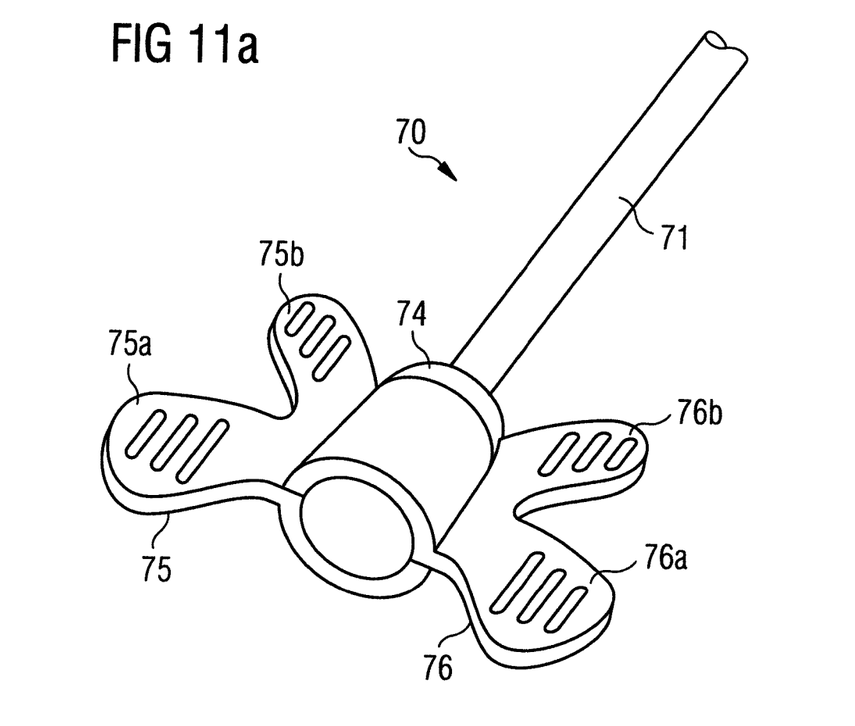
FIGS. 11a and 11b show another example of an introducer sheath in different views.
Figure 11B:
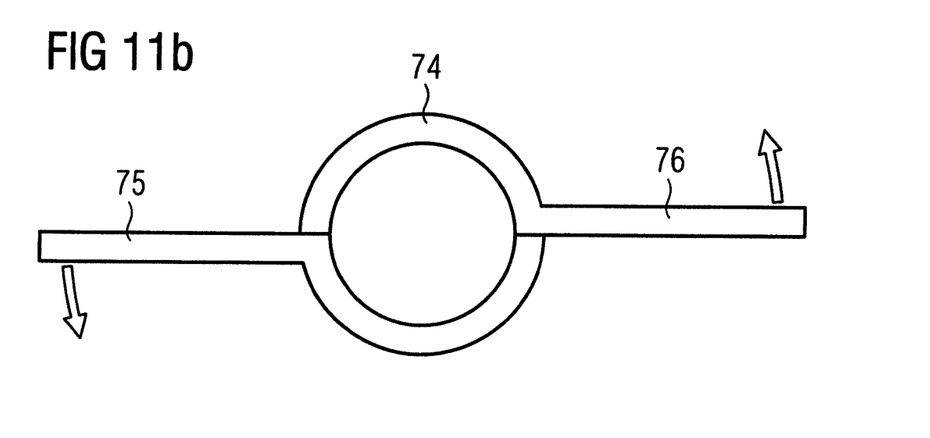

FIGS. 11a and 11b disclose another example of an introducer sheath 70 having a tubular body 71 and a hemostasis valve 74 that can be separated by means of handles 75 and 76. Each of the handles 75 and 76 has wings 75a, 75b and 76a, 76b, respectively. In order to apply a breaking force to the hemostasis valve 74 a user grips the handles 75 and 76 and twists them in opposite directions, as indicated by the arrows in FIG. 11b. Twisting of the handles 75 and 76 is facilitated by providing each handle with two wings, wherein the handles 75 and 76 are twisted about an axis of rotation that runs perpendicular to the longitudinal axis of the tubular body 71 and between the wings 75a and 75b, and 76a and 76b, respectively. For instance, referring to FIGS. 11a and 11b, wing 75a may be moved "downwards", while wing 75b is moved "upwards", whereas at the same time wing 76a is moved "upwards" and wing 76b is moved "downwards" to create a twisting movement. After an initial breaking force has been applied, the user pulls at the handles 75 and 76 further to completely separate the introducer sheath 70 into two pieces.

Figure 12:
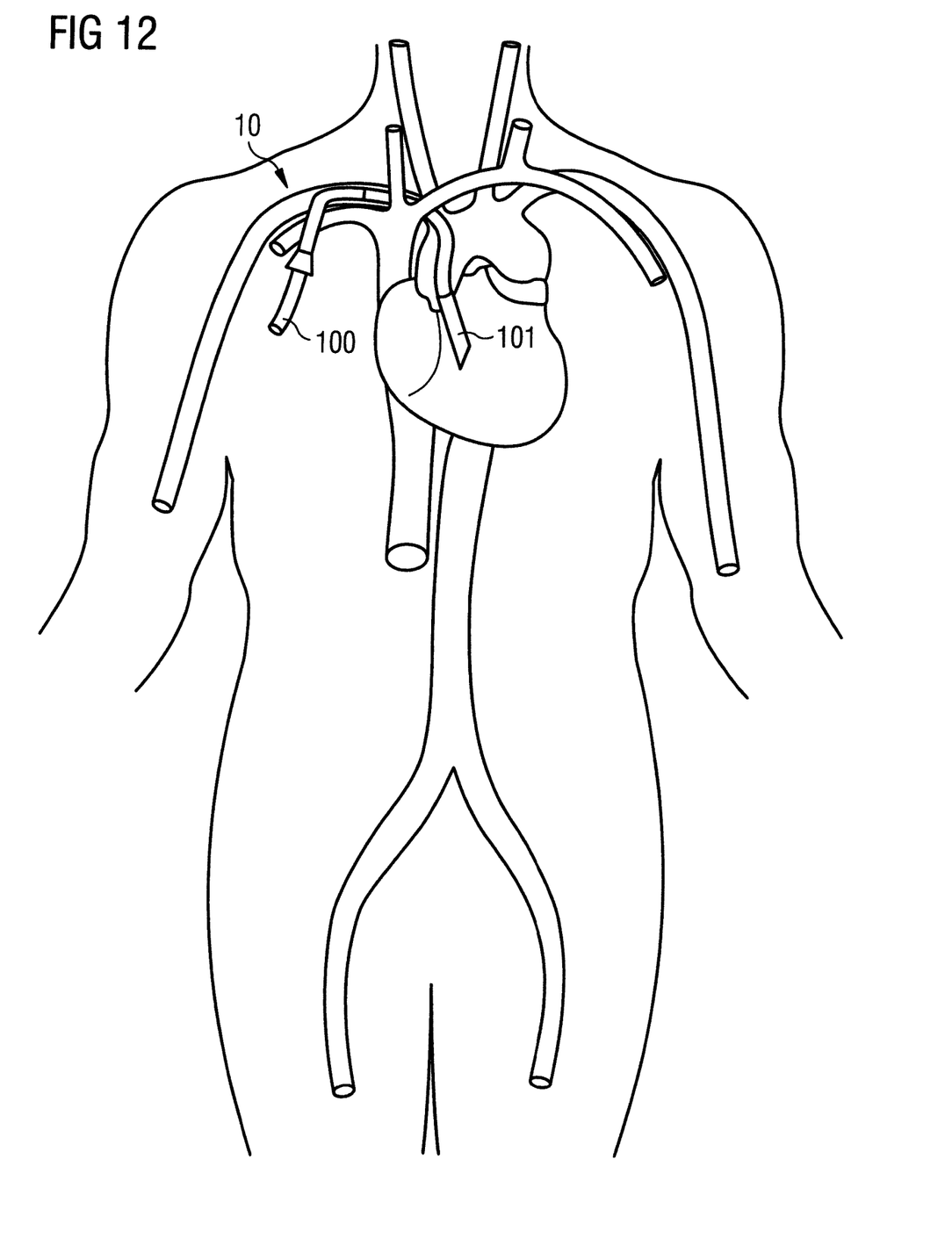
FIG. 12 shows an application of the invention.
Figure 13:
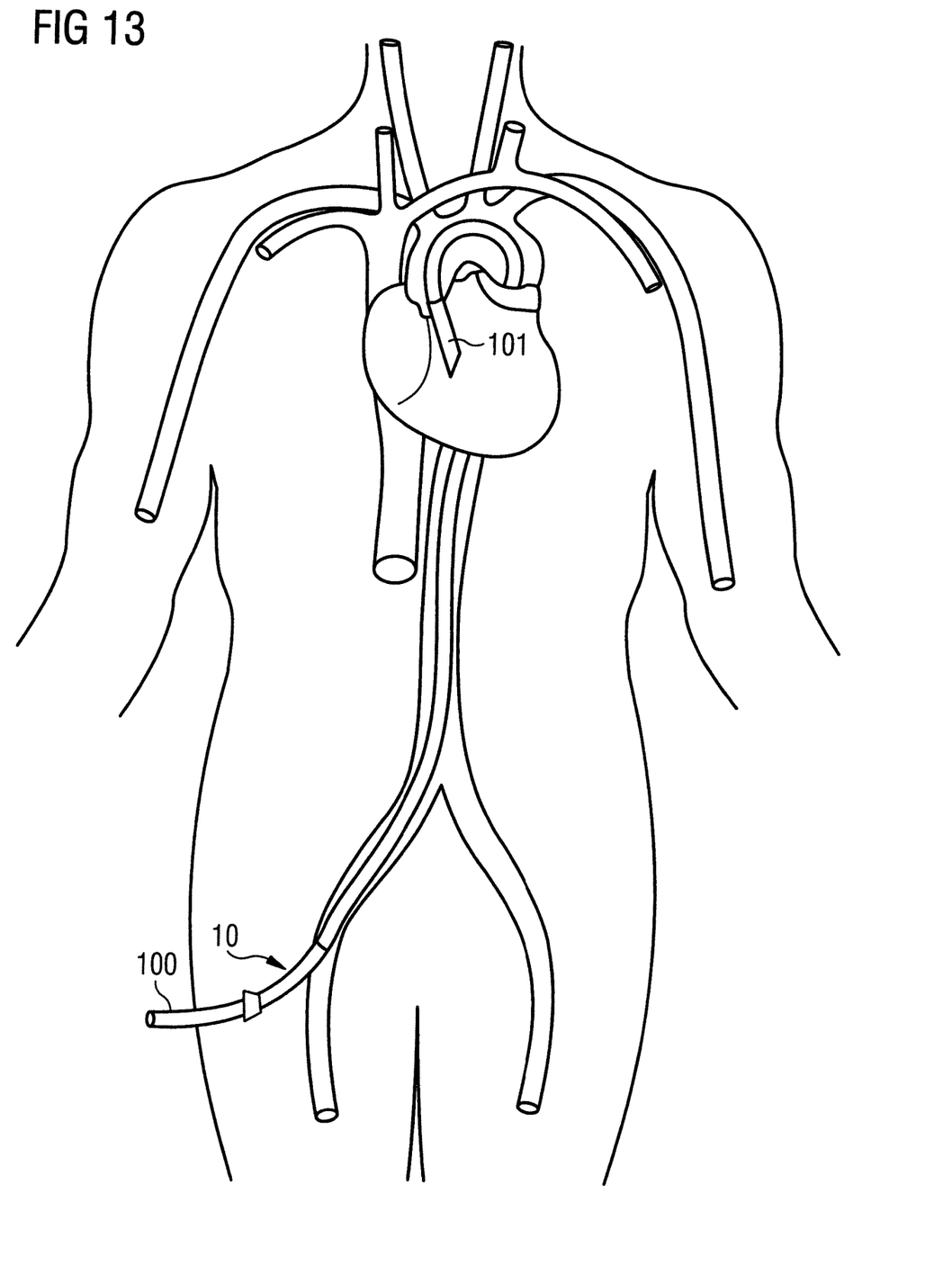
FIG. 13 shows another application of the invention.

Referring now to FIGS. 12 and 13, applications of an introducer sheath 10 are shown. The introducer sheath may be in accordance with any one of the above disclosed embodiments. It is used to insert an axial blood pump 101 by means of a catheter 100 through a patient's vessel into the patient's heart to provide a ventricular assist device. The vascular access may be placed in a peripheral vessel in the patient's thorax (FIG. 12) or in the patient's groin (FIG. 13).

Preferred Embodiments of the Invention

In the following paragraphs, preferred embodiments of the invention will be disclosed.

1. An introducer sheath 10 for providing access in a patient's body, comprising a tubular body 11 with a distal portion 12 and a proximal portion 13, the proximal portion 13 being configured to be inserted into the patient's body to allow a medical device 100 to be inserted through the introducer sheath 10 into the patient's body, the introducer sheath 10 being structured to facilitate separation along its length in a longitudinal direction, wherein the introducer sheath 10 further comprises at least a first handle 15 which is pivotable about a fulcrum 21, the first handle 15 having a first end portion 151 and a free second end portion 152 so as to form a lever, such that pivoting the handle 15 about the fulcrum 21 causes a contacting portion 23 of the handle to act on a respective counter portion 24 that is operatively connected to the distal portion 12 of the tubular body 11, thereby creating a breaking force that causes the distal portion 12 of the tubular body 11 to break.

2. The introducer sheath according to para. 1, wherein the fulcrum 21 is disposed eccentrically in the first end portion 151 of the first handle 15 and the contacting portion 23 is disposed at an edge of the first end portion 151, wherein a distance between the contacting portion 23 and the fulcrum 21 is less than a distance between the second end portion 152 of the first handle 15 and the fulcrum 21.

3. The introducer sheath according to para. 2, wherein a distance between the fulcrum 21 and the contacting portion 23 is larger than a distance between the fulcrum 21 and a portion of the edge of the first end portion 151 adjacent the contacting portion 23.

4. The introducer sheath according to para. 2 or 3, wherein the edge of the first end portion 151 of the first handle 15 is curved.

5. The introducer sheath according to para. 1, wherein the fulcrum 41 is disposed between the first and second end portions 351, 352 and the contacting portion 43 is disposed at an edge of the first end portion 351.

6. The introducer sheath according to para. 1, wherein the contacting portion is disposed between the first and second end portions and the fulcrum is disposed in the first end portion.

7. The introducer sheath according to any one of paras. 1 to 6, comprising a second handle 16, wherein the two handles 15, 16 are preferably diametrically opposed with respect to the tubular body 11.

8. The introducer sheath according to para. 7, wherein the second handle is fixedly attached to the distal portion of the tubular body.

9. The introducer sheath according to para. 7, wherein the first and second handles 15, 16 are pivotably attached to the distal portion 12 of the tubular body 11.

10. The introducer sheath according to any one of paras. 1 to 9, wherein the counter portion 45, 46 is part of the distal portion 32 of the introducer sheath 30.
11. The introducer sheath according to any one of paras. 7 to 10, wherein the counter portion is a contacting portion 24 of the second handle 26, wherein the contacting portion 24 of the second handle 16 preferably acts on the contacting portion 23 of the first handle 15. 12. The introducer sheath according to any one of paras. 1 to 11, wherein the first handle 15 is pivotably attached to the distal portion 12 of the tubular body 11 via a hinge, wherein the hinge preferably comprises at least one pin 81 arranged along the fulcrum 21 and at least one cavity 84 that receives the pin 81.
13. The introducer sheath according to any one of paras. 1 to 12, wherein the first handle 15 extends from the distal portion 12 of the tubular body 11 at an angle between 45° and 90°, preferably 60° and 80°, in an unstressed condition.
14. The introducer sheath according to any one of paras. 1 to 12, wherein the first handle 15" extends from the distal portion of the tubular body at an angle less than 45°, preferably between 10° and 30°, in an unstressed condition.
15. The introducer sheath according to any one of paras. 1 to 14, wherein the first handle 15 is pivotably attached to the distal portion 12 of the tubular body 11 such that pivoting in a direction towards the proximal portion 13 of the tubular body 11 causes the distal portion 12 to break.
16. The introducer sheath according to any one of paras. 1 to 14, wherein the first handle 15' is pivotably attached to the distal portion of the tubular body such that pivoting in a direction away from the proximal portion of the tubular body causes the distal portion to break.
17. The introducer sheath according to any one of paras. 1 to 16, wherein the first handle 15 comprises an engagement portion 19 configured to engage a locking member 18 such that the first handle 15 is prevented from pivoting.
18. The introducer sheath according to para. 17, further comprising a locking member 18, wherein the locking member 18 can be manipulated to be in or out of engagement with the engagement portion 19 of the first handle 15.
19. The introducer sheath according to para. 18, wherein the locking member 18 is engageable with the engagement portion 19 of the first handle 15 by means of threads, a hook or a clip.
20. The introducer sheath according to para. 18 or 19, wherein the locking member is a locking cap 18.
21. The introducer sheath according to any one of paras. 1 to 20, wherein at least the distal portion 12 of the tubular body 11 comprises a longitudinal notch 17 forming a predetermined breaking line.
22. The introducer sheath according to any one of paras. 1 to 21, comprising a hemostatic valve 14 in the distal portion 12 of the tubular body 11.
23. The introducer sheath according to para. 22, wherein the first handle 15 is attached to the hemostatic valve 14.

24. The introducer sheath according to any one of paras. 1 to 23, wherein the medical device comprises a catheter 100.
25. The introducer sheath according to para. 24, wherein the medical device comprises an axial blood pump 101 arranged at the tip of the catheter 100.

The invention claimed is:
1. An introducer sheath for providing access in a patient's body, comprising:
 a tubular body with a distal portion and a proximal portion, the proximal portion being configured to be inserted into the patient's body to allow a medical device to be inserted through the introducer sheath into the patient's body, the introducer sheath being structured to facilitate separation along its length in a longitudinal direction;
 a hemostatic valve in the distal portion of the tubular body; and
 a first handle and a second handle which extend from the hemostatic valve, each of the first and second handles comprising an eccentric fulcrum in a first end portion, each first end portion pivotally attached to the hemostatic valve, the hemostatic valve being separable by means of the first handle and the second handle, wherein the first handle and the second handle apply a torsional force to crack the hemostatic valve and cause the distal portion of the tubular body to break by rotation of the handles about their respective eccentric fulcrums.
2. The introducer sheath according to claim 1, wherein at least the distal portion of the tubular body comprises a longitudinal notch forming a predetermined breaking line.
3. The introducer sheath according to claim 1, wherein the introducer sheath further comprises longitudinal notches configured to facilitate splitting of the hemostatic valve into two pieces.
4. The introducer sheath according to claim 1, wherein the first handle and the second handle extend from the hemostatic valve at an angle of about 45°.
5. The introducer sheath according to claim 1, wherein the first handle and the second handle extend from the hemostatic valve asymmetrically in a top view of the introducer sheath.
6. The introducer sheath according to claim 1, wherein the medical device comprises a catheter.
7. The introducer sheath according to claim 6, wherein an axial blood pump is arranged at a tip of the catheter.
8. The introducer sheath of claim 1, wherein the first and second handle move toward each other when applying the torsional force.
9. The introducer sheath of claim 1, wherein the first and second handle move in opposite directions when applying the torsional force.

* * * * *